United States Patent [19]

Saito

[11] Patent Number: 5,049,685
[45] Date of Patent: Sep. 17, 1991

[54] NUCLEAR SUBSTITUTED SALICYLIC ACIDS AND THEIR SALTS

[75] Inventor: Toranosuke Saito, Osaka, Japan

[73] Assignee: Sanko Kaihatsu Kagaku Kenkyusho, Ibaraki, Japan

[21] Appl. No.: 434,808

[22] Filed: Nov. 9, 1989

[30] Foreign Application Priority Data

Nov. 22, 1988 [JP] Japan .......................... 63-293464
Feb. 3, 1989 [JP] Japan .......................... 1-24005

[51] Int. Cl.$^5$ .......................... C07F 3/00; C07F 3/06; C07F 15/00; C07F 7/00
[52] U.S. Cl. .......................... 556/132; 556/1; 556/147; 556/106; 556/184
[58] Field of Search .................. 556/121, 118, 1, 40, 556/41, 147, 184, 132, 105, 106

[56] References Cited

U.S. PATENT DOCUMENTS

| | | | |
|---|---|---|---|
| 2,974,171 | 3/1961 | Coffield | 556/121 X |
| 3,536,694 | 10/1970 | Webster | 556/121 X |
| 3,651,106 | 3/1972 | Harrison | 556/121 |
| 3,663,584 | 5/1972 | Alvarez | 556/121 |
| 4,173,650 | 11/1979 | Hanifin, Jr. et al. | 556/121 X |

*Primary Examiner*—Arthur C. Prescott
*Attorney, Agent, or Firm*—Jeffers, Hoffman & Niewyk

[57] ABSTRACT

A nuclear substituted salicylic acid represented by the following general formula (I):

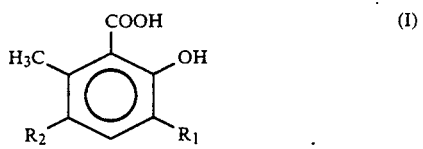

(in the formula (I), $R_1$ represents a methyl group, an isopropyl group, a tert-butyl group, a tert-amyl group, a tert-hexyl group, a tert-octyl group, an α, α-dialkylbenzyl group or a nuclear substituted α, α-dialkylbenzyl group; and $R_2$ represents a tert-butyl group, a tert-amyl group, a tert-hexyl group, a tert-octyl group, an α, α-dialkylbenzyl group or a nuclear substituted α, α-dialkylbenzyl group) and a salt thereof are herein disclosed. The novel nuclear substituted salicylic acids and salts thereof according to the present invention have good solubility in water, organic solvents or organic polymeric compounds and, therefore, these compounds are very favorable as bactericidal and germicidal agents, stabilizers for polymeric compounds or color developing agents for recording materials.

6 Claims, 7 Drawing Sheets

NUCLEAR SUBSTITUTED SALICYLIC ACIDS AND THEIR SALTS

BACKGROUND OF THE INVENTION

1. Field of the Invention

The present invention relates to a novel nuclear substituted salicylic acid and a salt thereof. The novel nuclear substituted salicylic acid and the salt thereof according to the present invention have good solubility in water, an organic solvent or an organic polymeric compound and are favorably used as germicidal or bactericidal agents, a stabilizer for polymeric compounds or a color developing agent for recording materials.

2. Description of the Prior Art

The nuclear substituted salicylic acids and their salts exhibit high germicidal or bactericidal effect and can be used as germicidal or bactericidal agents (see, for instance, Japanese Patent Laid-Open Application (hereunder referred to as "J.P. KOKAI") No. Sho 62-153245). Polyvalent metal salts of the nuclear substituted salicylic acids can be used as stabilizers for halogen atom-containing polymeric compounds such as polyvinyl chloride (see J.P. KOKAI No. Sho 56-112955). Moreover, the polyvalent metal salts of the nuclear substituted salicylic acids, in particular zinc salts thereof are employed as color developing agents for recording materials (see J.P. KOKAI Nos. Sho 48-98914; Sho 62-25086 and Sho 63-186729).

SUMMARY OF THE INVENTION

An object of the present invention is to provide specific nuclear substituted salicylic acids and their salts which have good solubility in water, an organic solvent or an organic polymeric compound and are favorably used as germicidal or bactericidal agents, a stabilizer for polymeric compounds or a color developing agent for recording materials.

The aforementioned object of the present invention can effectively be achieved by providing novel nuclear substituted salicylic acids represented by the following general formula (I):

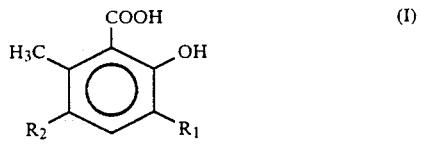

(in the formula (I), $R_1$ represents a methyl group, an isopropyl group, a tert-butyl group, a tert-amyl group, a tert-hexyl group, a tert-octyl group, an $\alpha,\alpha$-dialkylbenzyl group or a nuclear substituted $\alpha,\alpha$-dialkylbenzyl group; and $R_2$ represents a tert-butyl group, a tert-amyl group, a tert-hexyl group, a tert-octyl group, an $\alpha,\alpha$-dialkylbenzyl group or a nuclear substituted $\alpha$, $\alpha$-dialkylbenzyl group) and salts thereof.

BRIEF DESCRIPTION OF THE DRAWINGS

All of the attached

DETAILED DESCRIPTION OF THE INVENTION

Figure 1:
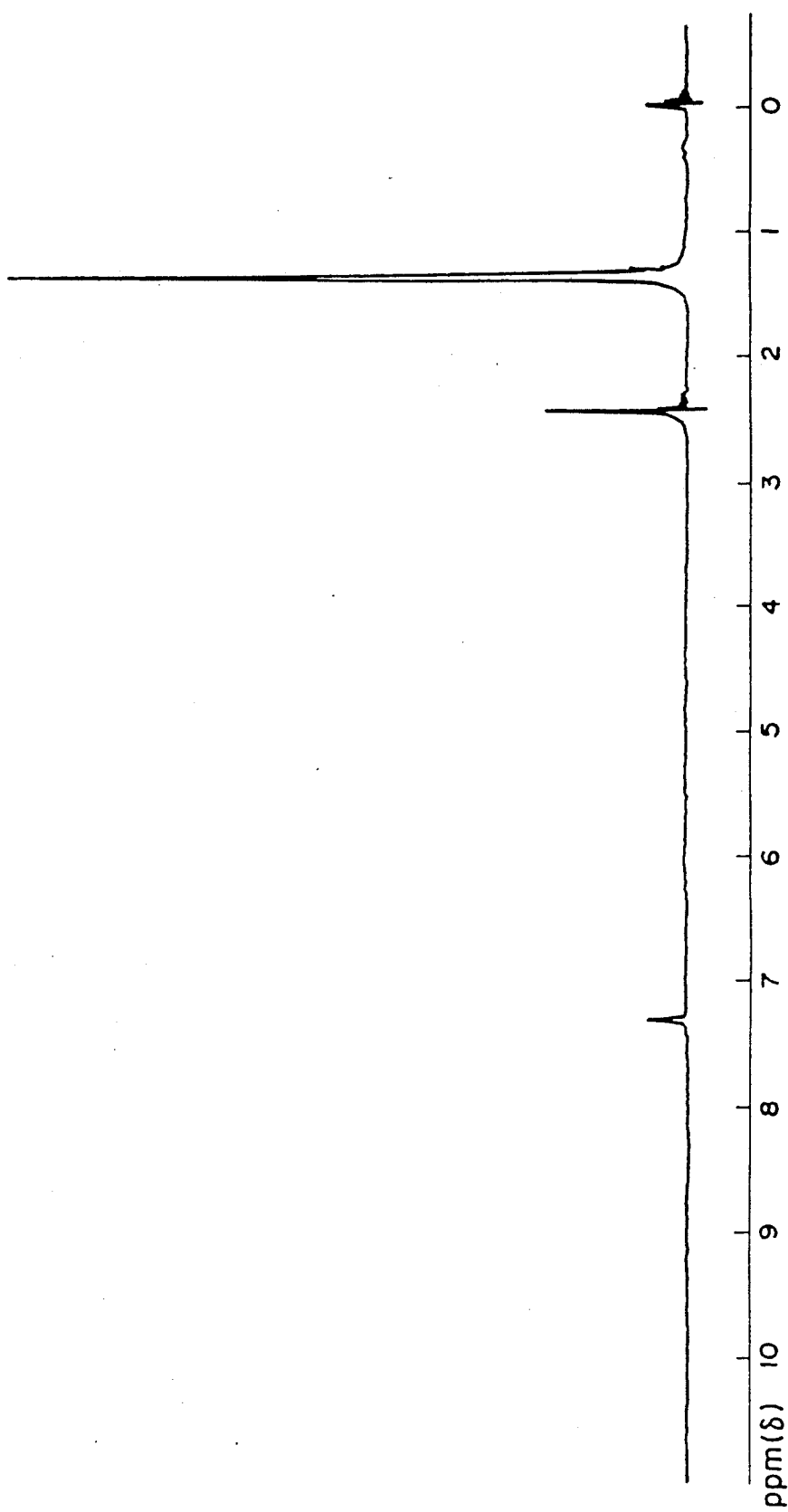
FIGS. 1 to 7 are charts NMR absorption spectroscopic measurement obtained on the nuclear substituted salicylic acids prepared in Examples 1, 2-2, 3-2, 4-3, 5-3, 11-2 and 12-2 respectively. The NMR spectrophotometer used is JNM-PMX 60 SI available from JEOL LTD. Solvents used are DMSO-$d_6$ (FIGS. 1 to 5) and CDCl$_3$ (FIGS. 6 and 7). In all of the NMR spectroscopic measurement, tetramethylsilane is used as the reference substance.

These nuclear substituted salicylic acids and the salts thereof are characterized in that they have very high solubility in water, organic solvents or organic polymeric compounds.

Germicidal or bactericidal agents preferably have good water solubility since it is easy to apply them in the form of formulations containing water as a dispersion medium. Alkali metal salts, amine salts or ammonium salts of the nuclear substituted salicylic acids represented by the general formula (I) are easily dissolved in water and, therefore, aqueous solutions thereof having a high concentration can be prepared therefrom. In addition, they do not exert photoallergy, in particular, on the skin and hence they are safe and suitable for wide use as germicidal and/or bactericidal agents.

Various kinds of metal compounds have been used as stabilizers for halogen atom-containing polymeric compounds and in particular if it is desired that a polymer composition be transparent, the metal compounds serving as the stabilizers are selected from those having good solubility in the polymeric compound interested. The polyvalent metal salts of the nuclear substituted salicylic acids represented by the general formula (I) have good solubility in, or highly compatible with the polymeric compounds, provide completely transparent compositions thereof and, in particular, impart excellent stability to heat and light to the polymer compositions.

A color developing reaction of a color developing agent for recording materials is generally carried out in an organic medium having a relatively low polarity. Therefore, it is believed that the most important property among those required for the color developing agent is the solubility in a medium used. The polyvalent metal salts of the nuclear substituted salicylic acids represented by the general formula (I), in particular zinc salts thereof have good solubility in organic solvents having a low polarity and exhibit a high color developing effect. Therefore, they have advantages such as excellent color developing capacity and color developing rate when they are used as color developing agents.

The solubility thereof in a specific solvent is closely related with the structure thereof represented by the general formula (I). In the general formula (I), $R_1$ is a methyl group, an isopropyl group, a tert-butyl group, a tert-amyl group, a tert-hexyl group, a tert-octyl group, an $\alpha$, $\alpha$-dialkylbenzyl group or a nuclear substituted $\alpha$, $\alpha$-dialkylbenzyl group; and $R_2$ is a tert-butyl group, a tert-amyl group, a tert-hexyl group, a tert-octyl group, an $\alpha$, $\alpha$-dialkylbenzyl group or a nuclear substituted $\alpha$, $\alpha$-dialkylbenzyl group and these bulky groups serve to increase the solubility of these nuclear substituted salicylic acids and the salts thereof in organic solvents or organic polymeric compounds. However, such an effect is still insufficient for attaining good solubility to the extent that the present invention intends to achieve. The most important structure feature of the compounds of the present invention is that a methyl group is present at 6-position of the nuclear substituted salicylic acids represented by the general formula (I) and it is surprising that the solubility of these compounds in organic solvents becomes quite high due to a synergistic effect of the presence of one methyl group at 6-position of the nuclear substituted salicylic acid and the bulky groups represented by $R_1$ and $R_2$. Thus, if the nuclear substituted salicylic acids have a methyl group at 6-position thereof and bulky groups ($R_1$ and $R_2$) at 3- and 5-positions respectively, there can be obtained such salicylic acid derivatives having good solubility in water, organic solvents or organic polymeric compounds. These compounds fall within the scope of the present invention.

Specific examples of the nuclear substituted salicylic acids represented by the general formula (I) include 3-6-dimethyl-5-($\alpha$, $\alpha$-dimethylbenzyl)salicylic acid, 3,6-dimethyl-5-($\alpha$, $\alpha$,3-trimethylbenzyl)salicylic acid, 3,6-dimethyl-5-($\alpha$, $\alpha$,4-trimethylbenzyl)salicylic acid, 3,6-dimethyl-5-($\alpha$-methyl-$\alpha$-ethylbenzyl)salicylic acid, 3-isopropyl-5-($\alpha$-dimethylbenzyl)-6-methylsalicylic acid, 3-isopropyl-5-($\alpha$-methyl-$\alpha$-ethylbenzyl)-6-methylsalicylic acid, 3,5-di-tert-butyl-6-methylsalicylic acid, 3-tert-butyl-5-tert-amyl-6-methylsalicylic acid, 3-tert-butyl-5-tert-hexyl-6-methylsalicylic acid, 3-tert-butyl-5-tert-octyl-6-methylsalicylic acid, 3-tert-butyl-5-($\alpha$, $\alpha$-dimethylbenzyl)-6-methylsalicylic acid, 3-tert-butyl-5-($\alpha,\alpha$,3-trimethylbenzyl)-6-methylsalicylic acid, 3-tert-butyl-5-( $\alpha,\alpha$,4-trimethylbenzyl)-6-methylsalicylic acid, 3-tert-butyl-5-($\alpha$-methyl-$\alpha$-ethylbenzyl)-6-methylsalicylic acid, 3-tert-amyl-5-tert-butyl-6-methylsalicylic acid, 3,5-di-tert-amyl-6-methylsalicylic acid, 3-tert-hexyl-5-tert-butyl-6-methylsalicylic acid, 3,5-di-tert-hexyl-6-methylsalicylic acid, 3-tert-octyl-5-tert-butyl-6-methylsalicylic acid, 3,5-di-tert-octyl-6-methylsalicylic acid, 3-($\alpha$, $\alpha$-dimethyl-benzyl)-5-tert-butyl-6-methyl-salicylic acid or 3,5-di-($\alpha$,-$\alpha$-dimethylbenzyl)-6-methyl-salicylic acid. However, examples thereof preferred are 3,6-dimethyl-5-($\alpha$, $\alpha$-dimethylbenzyl)salicylic acid, 3-isopropyl-5-($\alpha,\alpha$-dimethyl-benzyl)-6-methylsalicylic acid, 3,5-di-tert-butyl-6-methylsalicylic acid, 3-tert-butyl-5-($\alpha$, $\alpha$-dimethylbenzyl)-6-methylsalicylic acid, 3,5-di-tert-amyl-6-methylsalicylic acid, 3-tert-octyl-5-tert-butyl-6-methylsalicylic acid or 3-($\alpha$, $\alpha$-dimethylbenzyl)-5-tert-butyl-6-methylsalicylic acid from the viewpoint of easiness of industrial enforcement and in the light of the purposes of the present invention.

The nuclear substituted salicylic acid represented by the general formula (I) can be prepared, in the form of a sodium salt or a potassium salt thereof, by reacting a sodium or potassium salt of a nuclear substituted phenol represented by the following general formula (II):

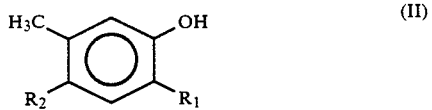

(II)

(wherein $R_1$ and $R_2$ are the same as those defined above in connection with the general formula (I) with carbon dioxide (Kolbe-Schmitt reaction). The sodium and potassium salts of the compounds represented by the general formulas (I) and (II) have good solubility in a variety of organic solvents. Therefore, it is desirable to perform a series of the operations for preparing the intended compounds in an organic solvent. The reaction temperature preferably ranges from 120° to 200° C.

The nuclear substituted phenols represented by the general formula (II) can be prepared through a nuclear substitution reaction of m-cresol. As an agent for introducing substituents into the nucleus of phenol, there may be listed, for instance, propylene, isobutylene, tert-butyl chloride, tert-butanol, 2-methyl-1-butene, 2-methyl-2-butene, 2-methyl-1-pentene, 2-methyl-2-pentene, 2-ethyl-1-hexene, di-isobutylene, $\alpha$-methylstyrene, $\alpha$,3-dimethylstyrene, $\alpha$,4-dimethylstyrene, $\alpha$-ethylstyrene, $\alpha,\beta$-dimethylacid styrene, $\alpha$-methyl-$\beta$-propylstyrene or $\alpha,\beta$-diethylstyrene. Preferred examples of catalysts for the introduction of such substituents are acidic catalysts such as sulfuric acid, methanesulfonic acid, trifluoromethanesulfonic acid, p-toluenesulfonic acid, xylenesulfonic acid, sec-butylbenzenesulfonic acid, heteropolyacid, boron trifluoride, aluminum chloride or zinc chloride. If $R_1$ and $R_2$ in the general formula (I) or (II) are the same, these substituents can be introduced into m-cresol with one agent at the same time. On the contrary, if these substituents are different from one another, $R_1$ is first introduced and subsequently $R_2$ is introduced.

As has been described above, the nuclear substituted salicylic acids according to the present invention are prepared in the form of their sodium or potassium salts. To prepare free nuclear substituted salicylic acids, diluted sulfuric acid or diluted hydrochloric acid is added to an aqueous solution of the salicylic acids to thus acid-decompose the salt. The resultant free acid product may be recrystallized from an organic solvent to purify the same. These free salicylic acids are in general insoluble in water, but sufficiently soluble in organic solvents. Therefore, they are used as oil-soluble mildew proofing agents for cutting oils.

Since alkali metal salts, amine salts or ammonium salts of the nuclear substituted salicylic acids are soluble in water, aqueous solutions thereof can be obtained by neutralizing the corresponding free nuclear substituted salicylic acid with an alkali hydroxide, an amine or ammonia in an aqueous medium. Examples of preferred alkali hydroxides are lithium hydroxide, sodium hydroxide and potassium hydroxide; examples of preferred amines are methylamine, dimethylamine, trimethylamine, ethylamine, diethylamine, triethylamine, ethanolamine, diethanolamine, triethanolamine, isopropanolamine, diisopropanolamine, triisopropanolamine, dimethylaminoethanol, diethylaminoethanol or morpholine. These water-soluble nuclear substituted salicylic acid salts have applications as water soluble antibacterial agents or mildew proofing agents.

Polyvalent metal salts of the nuclear substituted salicylic acids are hardly soluble or insoluble in water, but sufficiently soluble in organic solvents or organic polymeric compounds. These polyvalent metal salts are prepared from an aqueous solution of a water-soluble salt of the nuclear substituted salicylic acid and an aqueous solution of a water-soluble polyvalent metal salt in the form of a water-insoluble salts according to a double decomposition technique. During the preparation, heat can be applied or an organic solvent can be added to the reaction, if necessary. Examples of preferred polyvalent metals are magnesium, aluminum, calcium, iron, cobalt, nickel, zinc, strontium, cadmium, tin, barium or lead, in particular magnesium, calcium and zinc. Examples of water-soluble polyvalent metal salts are magnesium sulfate, aluminum sulfate, calcium chloride, zinc sulfate and lead acetate. The polyvalent metal salts of the nuclear substituted salicylic acids, in particular magnesium, calcium and zinc salts are used as stabilizers for chlorine atom-containing polymeric compounds. In such cases, it is preferred that the substituents $R_1$ and $R_2$ in the general formula (I) are different from one another. This is because such compounds have high solubility. In addition, the polyvalent metal salts of the nuclear substituted salicylic acids, in particular zinc salts thereof are employed as color developing agents for recording materials. In such cases, if the total number of carbon atoms of the substituents $R_1$ and $R_2$ in the general formula (I) is preferably not less than 9 and more preferably not less than 12, they impart good water resistance or moisture resistance to recorded images.

The present invention will hereunder be described with reference to the following specific Examples and Reference Examples in order to make the present invention more clearer.

EXAMPLE 1

To a 2,000 ml three-necked flask of a hard glass equipped with a stirring machine, a thermometer and a reflux condenser capable of separating and removing water, there were charged 330 g (1.5 mole) of 2,4-di-tert-butyl-5-methylphenol, 1,000 g of diethylene glycol dimethyl ether, 100 g of toluene and 120 g of 50% aqueous solution of sodium hydroxide. The contents of the flask was heated with stirring and water was removed as an azeotropic mixture with toluene. The contents of the flask from which water was removed were transferred to a stainless steel autoclave having an inner volume of 2,000 ml. The autoclave was supplied with carbon dioxide gas under a pressure of 20 kg/cm$^2$ and the reaction was continued at 180° C. for 3 hours. The autoclave was cooled till the temperature of the contents was not more than 90° C., thereafter the pressure of the autoclave was released to ordinary pressure and the contents were transferred to a beaker having an inner volume of 5,000 ml. To the contents, there were added 3,000 g of hot water and 500 g of toluene and the mixture was stirred. The mixture was allowed to stand and an oil layer separated therefrom as an upper layer was removed. 170 Milliliters of 10N diluted sulfuric acid solution was gradually added thereto with stirring. The solution was cooled to precipitate crystals, followed by filtering off the resulting crystals and then recrystallizing the precipitates from 600 ml of toluene to thus obtain 262 g of white crystals. it is confirmed that the product is 3,5-di-tert-butyl-6-methyl salicylic acid, from its physical and chemical properties: melting point 178° C.; acid value =210.9 (calculated value '212.2) and NMR absorption spectra (see FIG. 1).

EXAMPLE 2-1

To a 1,000 ml four-necked flask of a hard glass equipped with a stirring machine, a thermometer, a reflux condenser and a dropping funnel, there were charged 492 g (3 moles) of 2-tert-butyl-5-methylphenol and 10 g of dehydrated p-toluenesulfonic acid. The flask was cooled so that the temperature was maintained to about 30° to 35° C. 319 Grams (2.7 moles) of α-methylstyrene was dropwise added to the flask over about 10 hours with vigorous stirring. Additional 10 hours after the completion of the dropwise addition, 200 g of water was added thereto, the temperature was raised with stirring and the contents were boiled for about one hour. The contents were transferred to a separatory funnel to remove water phase and the remaining phase was washed with 200 g each of hot water three times. it was transferred to a vacuum distillation apparatus having an inner volume of 1,000 ml and about 610 g of the fraction distilled out between 153° to 158° C. under 1.5 Torr was collected. It s confirmed that the product thus obtained is 2-tert-butyl-4-(α, α-dimethylbenzyl)-5-methylphenol from its physical and chemical properties: melting point =92° C.; hydroxyl value 199.1 (calculated value =198.7).

EXAMPLE 2-2

Figure 2:
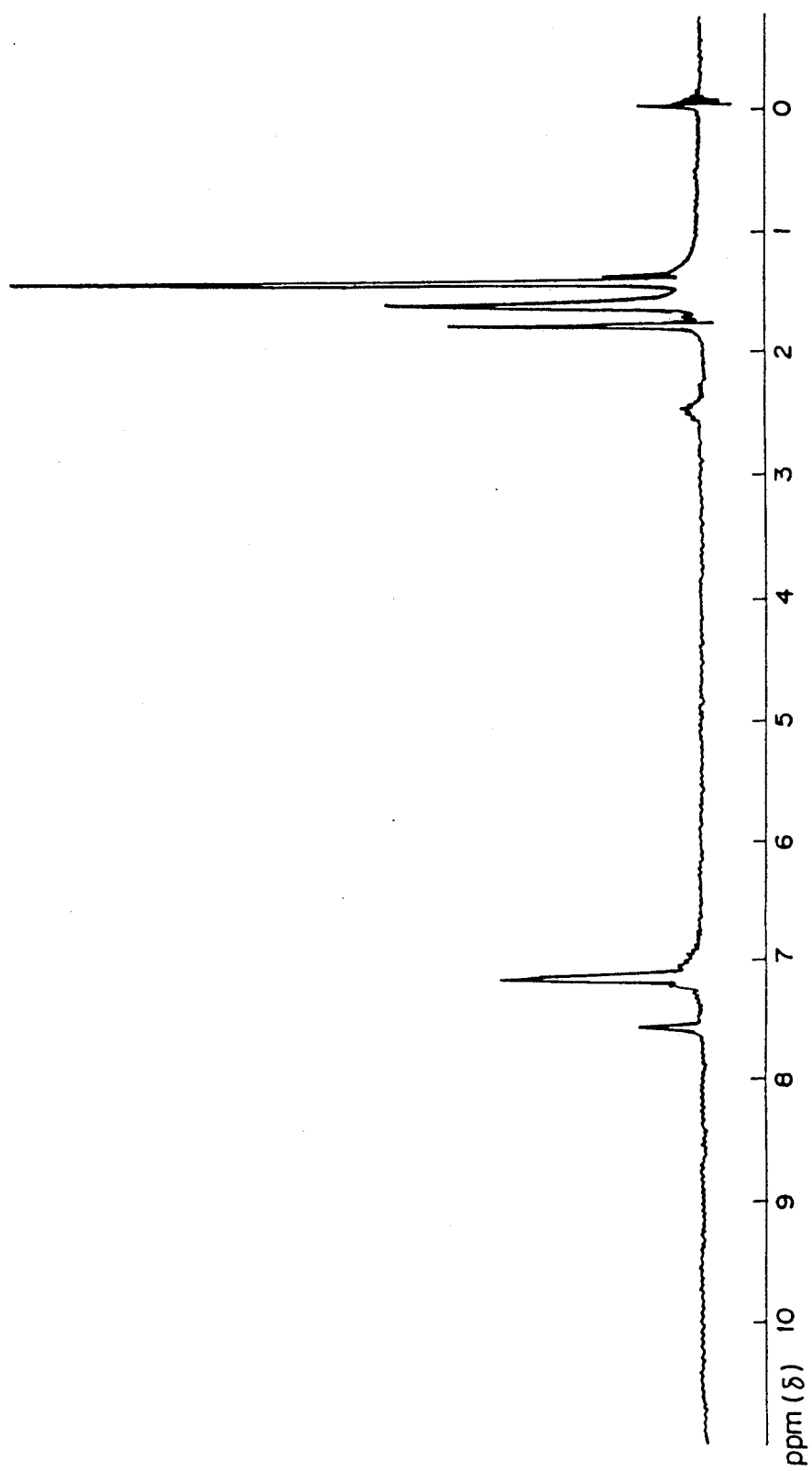

To a 2,000 ml three-necked flask of a hard glass equipped with a stirring machine, a thermometer and a reflux condenser capable of separating and removing water, there were added 423 g (1.5 mole) of 2-tert-butyl-4-(α, α-dimethylbenzyl)-5-methylphenol prepared in Example 2-1, 800 g of diethylene glycol dimethyl ether, 350 g of toluene and 120 g of 50% aqueous solution of sodium hydroxide. The flask was heated with stirring to remove water as an azeotropic mixture with toluene. The contents of the flask from which water was removed were transferred to a stainless steel autoclave having an inner volume of 2,000 ml. The autoclave was supplied with carbon dioxide gas under a pressure of 20 kg/cm$^2$, and the reaction was continued at 180° C. for 3 hours. The autoclave was cooled till the temperature of its contents was reduced to not more than 90° C., thereafter the pressure of the autoclave was released to ordinary pressure and the contents were transferred to a flask having an inner volume of 10,000 ml. To the contents, there were added 5,000 g of water, the temperature of the mixture was raised to 85° C. with stirring, then the mixture was allowed to stand. After an oil layer i.e., an upper layer was removed, 170 ml of 10N diluted sulfuric acid solution was gradually added thereto with stirring. Oily substances were separated and it was cooled to precipitate out crystals. Then, they were recrystallized from n-hexane to thus obtain 368 g of white crystals. it is confirmed that the product is 3-tert-butyl-5-(α, α-dimethylbenzyl)-6-methyl salicylic acid, from its physical and chemical properties: melting point 172° C.; an acid value =172.2 (calculated value =171.9) and NMR absorption spectra (see FIG. 2).

EXAMPLE 3-1

To a 1,000 ml four-necked flask of a hard glass equipped with a stirring machine, a thermometer, a dropping funnel and a reflux condenser, there were added 378 g (3.5 moles) of m-cresol and 5 g of xylenesulfonic acid. 420 Gram (3 moles) of 2-methyl-2-butene containing a small amount of 2-methyl-1-butene was dropwise added to the contents of the flask over about 10 hours with vigorous stirring. As the temperature of the contents was raised due to the heat of reaction during the dropwise addition, the flask was cooled so as to maintain the temperature to 30° to 35° C. Additional 10 hours after the dropwise addition, 200 g of water was added and the mixture was heated with stirring to continue boiling thereof for about one hour. The reaction solution was transferred to a separatory funnel to remove the water phase and further the remaining phase was washed with 200 ml each of hot water three times. The washed solution was introduced into a vacuum distillation apparatus and 510 g of the fraction distilled off between 110° to 120° C. under a pressure of 1 Torr was collected. it is confirmed that the product is 2,4-di-tert-amyl-5-methylphenol from its physical and chemical properties: melting point =64° C.; hydroxyl value=226.5 (calculated value =225.9).

EXAMPLE 3-2

Figure 3:
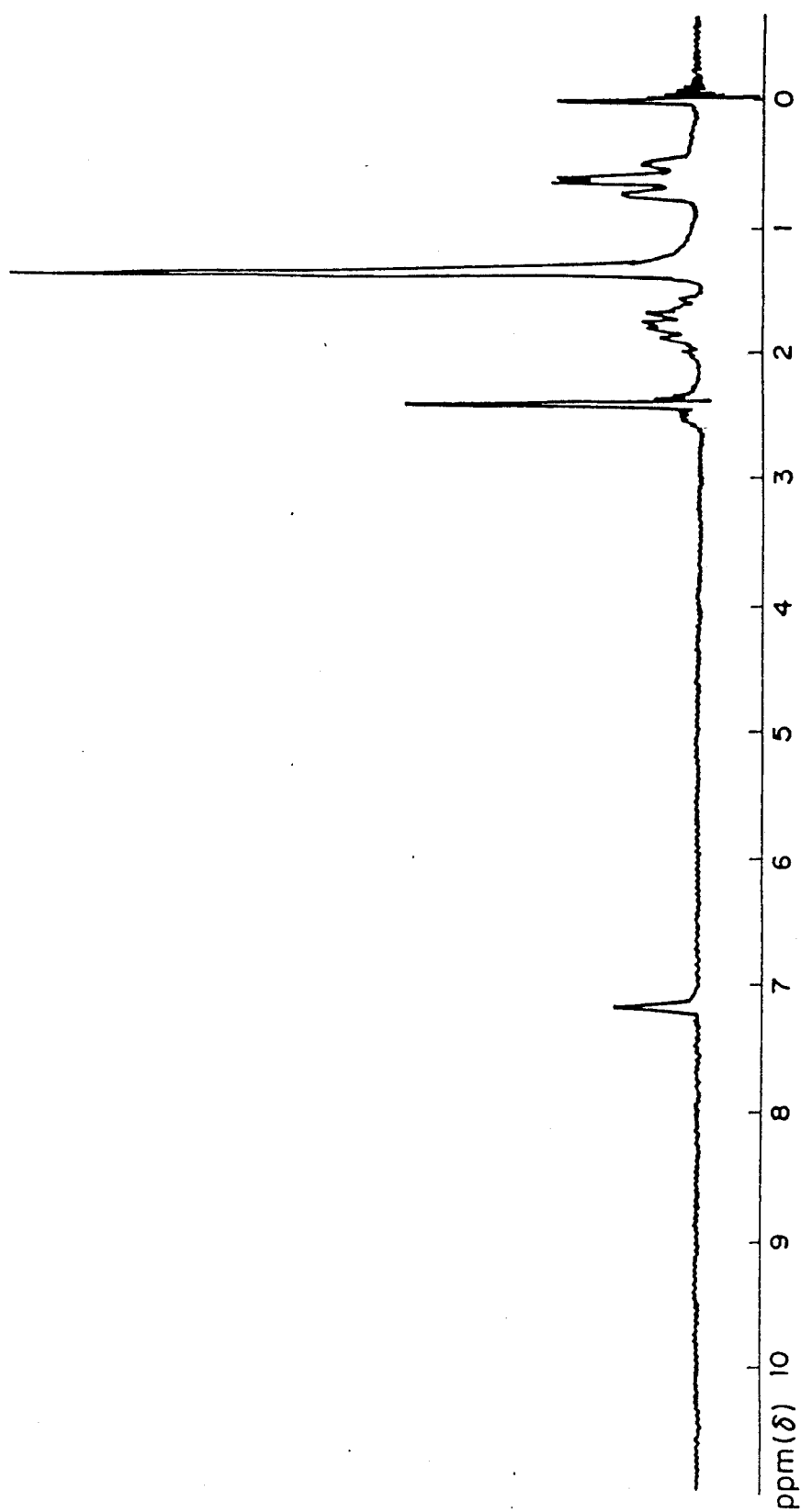

According to the same procedures as used in Example 1, 278 g of white crystals were obtained from 372 g (1.5 mole) of 2,4-di-tert-amyl-5-methylphenol prepared in Example 3-1. It is confirmed that this product is 3,5-di tert-amyl-6-methyl-salicylic acid from its physical and chemical properties: melting point = 125° C.; acid value = 193.0 (calculated value '191.9); and NMR absorption spectra (see FIG. 3).

Example 4-1

According to the same procedures used in Example 3-1, 590 g of the fraction distilled off between 100° to 105° C. under a pressure of 1.5 Torr from 540 g (5 moles) of m-cresol and 336 g (3 moles) of di-isobutylene. This was a slightly viscous colorless transparent liquid and had a hydroxyl value of 253.5 (calculated value =254.6). In addition, it is confirmed that the product was 2-tert-octyl-5-methylphenol containing about 0.5% of 3-methyl-4-tert-octylphenol from gas chromatography measurement.

EXAMPLE 4-2

To a 1,000 ml four-neked flask of a hard glass equipped with a stirring machine, a thermometer, a port for blowing gases and a reflux condenser which was connected to a dry ice-trap at its top, there were added 550 g (2.5 moles) of 2-tert-octyl-5-methylphenol obtained in Example 4-1 and 5 g of sec-butylbenzenesulfonic acid. Isobutylene was blown through the gas blowing-port with stirring. Since heat was generated as the reaction proceeded, the flask was cooled so as to maintain the temperature of the contents to 30° to 45° C. The progress of the reaction was monitored by sometimes withdrawing the contents of the flask and subjecting them by gas chromatography analysis. Isobutylene was blown so that it took about 20 hours to sufficiently proceed the reaction. After the intended reaction was finished, the blowing of isobutylene was stopped and the contents were washed with hot water. The contents were a reddish-brown transparent liquid and its hydroxyl value was 192.4 (calculated value =202.9). It is considered that the difference between the calculated and found hydroxyl values resulted from impurities such as polymers of isobutylene. Moreover, it is confirmed that the product is 2-tert-octyl-4-tert-butyl-5-methylphenol having a purity of 93% from the gas chromatography measurement. In addition, the product was further purified to obtain a pure product and its melting point was found to be 72° C.

EXAMPLE 4-3

Figure 4:
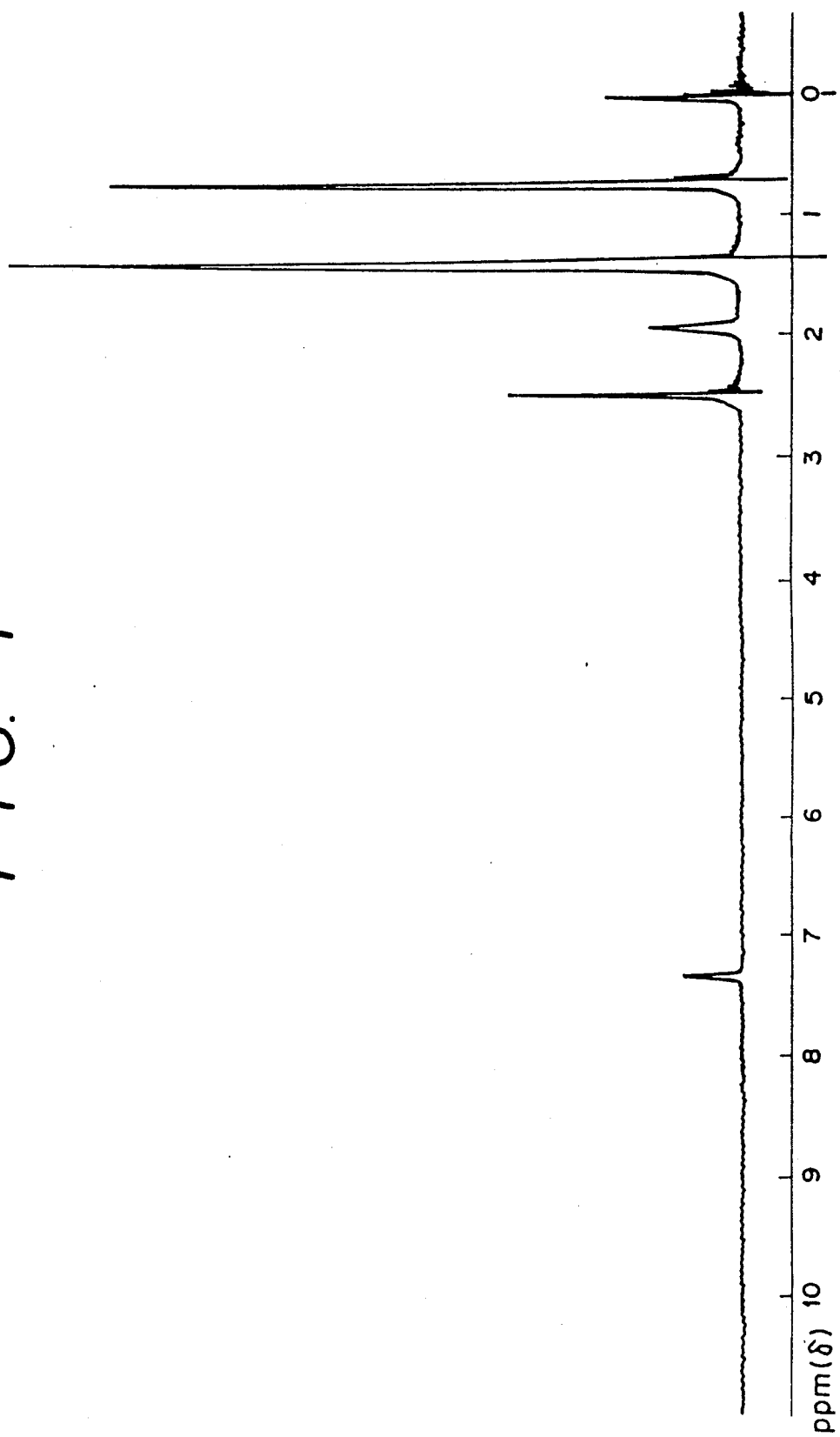

According to the same procedures as used in Example 2-2, 341 g of white crystals were obtained from 60% (1.5 mole) of the product of Example 4-2. The product had a melting point of 165° C. and an acid value of 176.4 (calculated value = 175.1). In addition, the NMR absorption spectra thereof are as shown in FIG. 4. It is thus confirmed that the product is 3-tert-octyl-5-tert-butyl-6-methylsalicylic acid, i.e., 3-(1,1,3,3-tetramethylbutyl)-5-tert-butyl-6-methylsalicylic acid from the foregoing physical and chemical properties.

EXAMPLE 5-1

According to the same procedures used in Example 3-1, 618 g of the fraction distilled off between 105° to 115° C. under a pressure of 1 Torr from 540 g (5 moles) of m-cresol and 354 g (3 moles) of α-methylstyrene. This product was approximately colorless quite viscous liquid and its hydroxyl value was 245.9 (calculated value = 247.9). In addition, it is confirmed that the product is 2-(α,α-dimethylbenzyl)-5-methophenol containing 1.3 % of 3-methyl-4-(α,α-dimethylbenzyl) phenol from the gas chromatography measurement.

EXAMPLE 5-2

According to the same procedures used in Example 4-2, there was obtained a light-brown quite viscous liquid from 565 g (2.5 moles) of 2-( α, α-dimethylbenzyl)-5-methylphenol obtained in Example 5-1. The hydroxyl value thereof was 187.2 (calculated value 198.7) and it is confirmed that the product is 2-(α, α-dimethylbenzyl)-4-tert-butyl-5-methylphenol having a purity of 94 % from the gas chromatography measurement.

EXAMPLE 5-3

Figure 5:
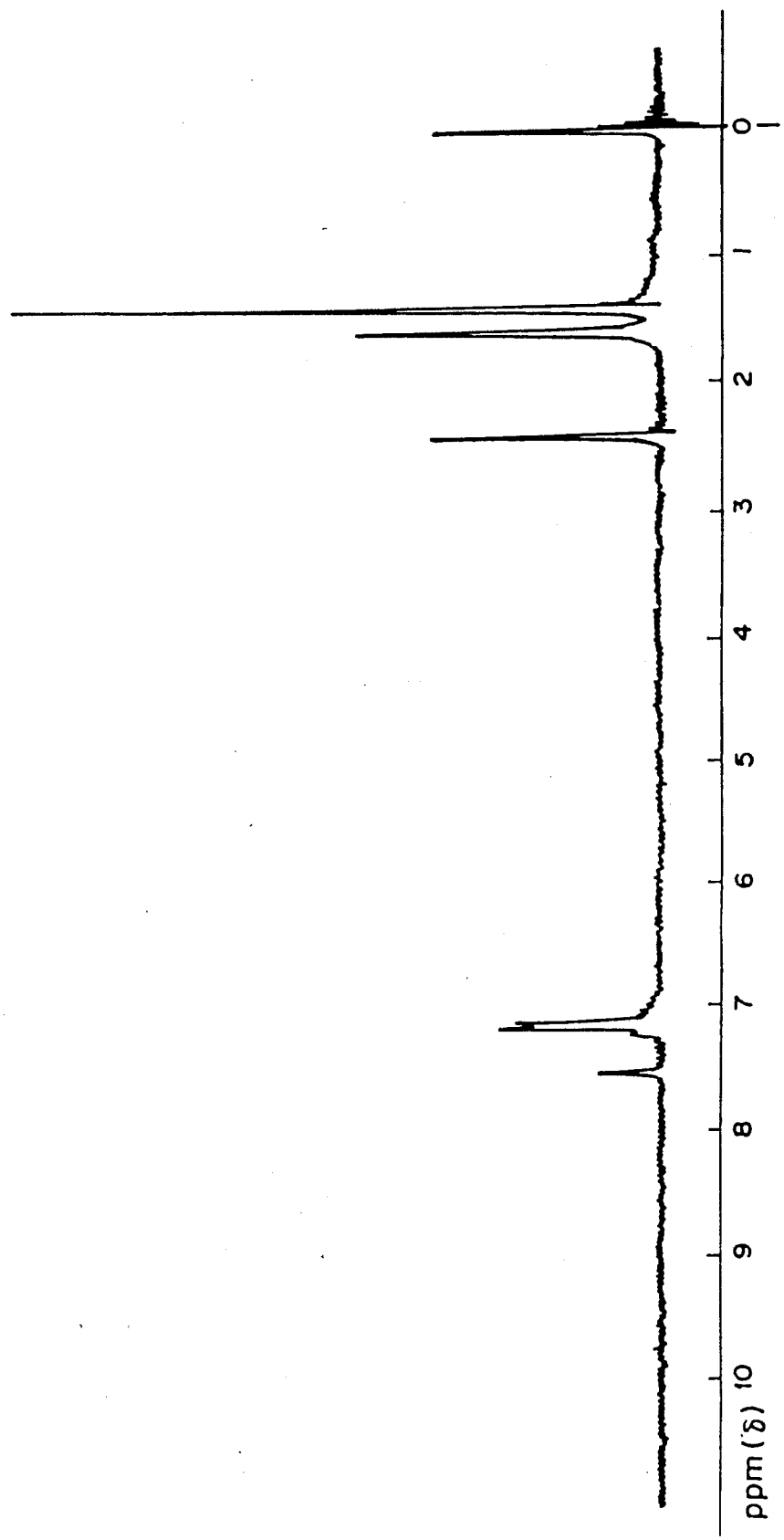

The same procedures used in Example 4-3 were repeated except that 2-( α, α-dimethylbenzyl)-4-tert-butyl-5-methylphenol obtained in Example 5-2 was used to thus obtain 362 g of white crystals. The product had a melting point of 181° C. and an acid value of 170.2 (calculated value = 171.9) and the NMR absorption spectra thereof were as shown in FIG. 5. It is confirmed that it is 3-(α, α-dimethylbenzyl)-5-tert-butyl-6-methyl salicylic acid from the foregoing physical and chemical properties.

EXAMPLE 6

264 Grams (1 mole) of 3,5-di-tert-butyl-6-methylsalicylic acid obtained in Example 1 was dissolved in 700 g of an aqueous solution containing one mole of sodium hydroxide. The resulting solution was an aqueous solution containing about 30% of sodium 3,5-di-tert-butyl-6-methylsalicylate.

EXAMPLE 7

According to the same procedure used in Example 6, sodium salts of the nuclear substituted salicylic acids obtained in Examples 2-2, 3-2, 4-3 and 5-3 were likewise prepared from the corresponding nuclear substituted salicylic acids.

EXAMPLE 8

According to the same procedure used in Example 6 except that an aqueous solution of triethanolamine or morpholine was substituted for the sodium hydroxide aqueous solution to thus prepare triethanolamine or morpholine salts of the corresponding nuclear substituted salicylic acids.

EXAMPLE 9

400 Grams of 25% zinc sulfate aqueous solution was introduced into a stainless steel beaker having an inner volume of 2,000 ml and whole the aqueous solution of sodium 3,5-di-tert-butyl-6-methylsalicylate obtained in Example 6 was poured into the beaker over 20 minutes with vigorous stirring. After stirring the mixture for additional 20 minutes, zinc 3,5-di-tert-butyl-6-methylsalicylate precipitated out from the solution was filtered off and the precipitates were washed with 1,000 ml of water. The precipitates were vacuum dried at a temperature of 110° C. to obtain 297 g of white powder. The zinc content of the product was 10.9% (calculated value = 11.0%). This confirms that the product is zinc salt of 3,5-di-tert-butyl-6-methylsalicylic acid.

EXAMPLE 10

According to the same procedures used in Example 9, pure-white powder was obtained from the sodium nuclear substituted salicylates prepared in Example 7 and it was confirmed that the products were zinc salts of the corresponding nuclear substituted salicylates from their zinc contents.

COMPARATIVE EXAMPLE 1 (SALTS OF 3,5-DI-TERT-BUTYLSALICYCLIC ACID)

According to the same procedures used in Examples 6, 8 and 9, sodium, morpholine and zinc salts of 3,5-di-tert-butyl salicylic acid were prepared from the salicylic acid.

EXAMPLE 11-1

To a 1,000 ml four-necked flask of a hard glass provided with a stirring machine, a thermometer, a dropping funnel and a reflux condenser, there were added 366 g (3 moles) of 2,5-xylenol and 3 g of p-toluenesulfonic acid. When the flask was heated, the contents thereof were molten at a temperature of not less than 75° C. At this stage, stirring of the contents was started and 295 g (2.5 moles) of α-methylstyrene was dropwise added to the contents from the dropping funner over about 4 hours while maintaining its temperature to 75° to 80° C. One hour after the completion of the dropwise addition, 200 ml of toluene and 200 ml of water from the dropping funnel were continuously added thereto and the contents were heated to their boiling point. The boiled contents were transferred to a separatory funnel and the acidic water phase separated therefrom as the lower phase was removed. Further, 200 ml of hot water was added to the separatory funnel to wash the contents, the washing operation was repeated three times. The oil phase was transferred to a vacuum distillation apparatus and thus about 520 g of the fraction which was distilled out between 145° to 148° C. at a pressure of about one Torr recovered. The fraction was recrystallized from toluene to obtain 370 g of white crystals having a melting point of 64° C. The hydroxyl value of this product was 232 (calculated value = 233.45). The product was confirmed to be 2,5-dimethyl-4-(α,α-dimethylbenzyl)phenol from the foregoing physical and chemical properties.

EXAMPLE 11-2

Figure 6:
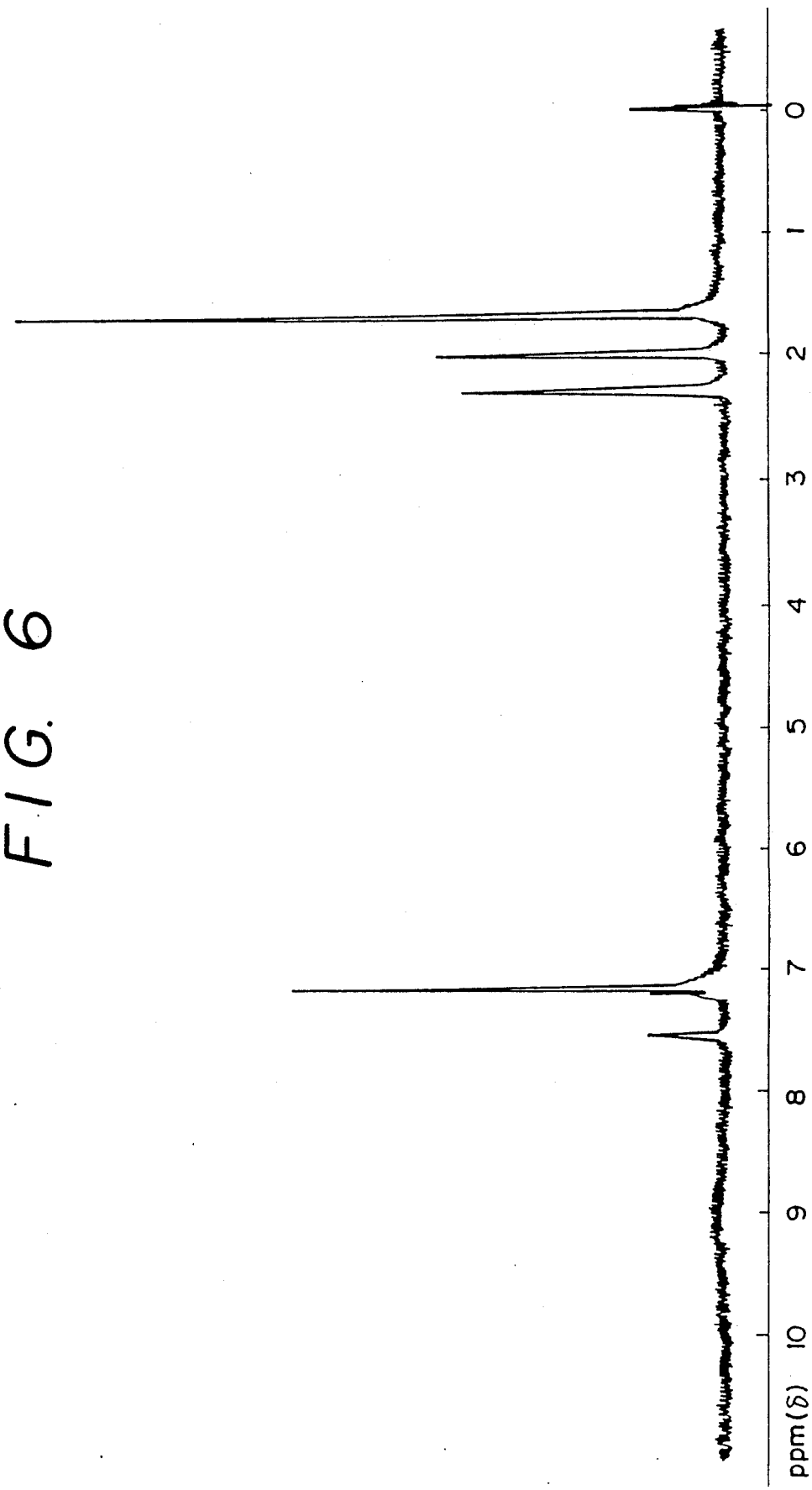

To a 1,000 ml three-necked flask of a hard glass equipped with a stirring machine, a thermometer and a reflux condenser capable of separating and removing water, there were added 300 g (1.25 mole) of 2,5-dimethyl-4-(α, α-dimethylbenzyl)phenol, 500 g of sulfolane, 100 g of toluene and 140 g of 50% potassium hydroxide solution. The flask was heated with stirring to remove water as an azeotropic mixture with toluene. The contents of the flask from which water was removed were transferred to an autoclave having an inner volume of 1,000 ml. The autoclave was supplied with carbon dioxide gas under a pressure of 20 kg/cm$^2$ to carry out the reaction at 160° C. for 6 hours. The autoclave was cooled till the temperature of the contents decreased to not more than 90° C. At this time, the pressure in the autoclave was released to ordinary pressure, followed by transferring the contents of the flask to a flask having an inner volume of 5,000 ml, adding 3,000 ml of hot water and 500 ml of toluene thereto, stirring the mixture and then allowing it to stand. After completely removing the upper toluene phase, 350 g of 20% diluted sulfuric acid solution was added. The crystals separated out from the solution was filtered off and the crystals were recrystallized from toluene to obtain 220 g of white crystals. The product had a melting point of 208° C. and the acid value of 196.6 (calculated value 197.31) and the result of the NMR spectroscopic measurement was shown in FIG. 6. These physical and chemical properties clearly confirm that the product is the intended 3,6-dimethyl-5-(α, α-dimethylbenzyl)salicylic acid.

EXAMPLE 12-1

According to the same procedures used in Example 11-1, 480 g of white crystals were obtained from 450 g (3 moles) of thymol (2-isopropyl-5-methylphenol) and 295 g (2.5 moles) of α-methylstyrene. Its melting point was 96° C. and the hydroxyl value thereof was 207.6 (calculated value = 209.05). This product is confirmed to be 2-isopropyl-4-(α,α-dimethylbenzyl)-5-methylphenol from the foregoing physical and chemical properties.

EXAMPLE 12-2

Figure 7:
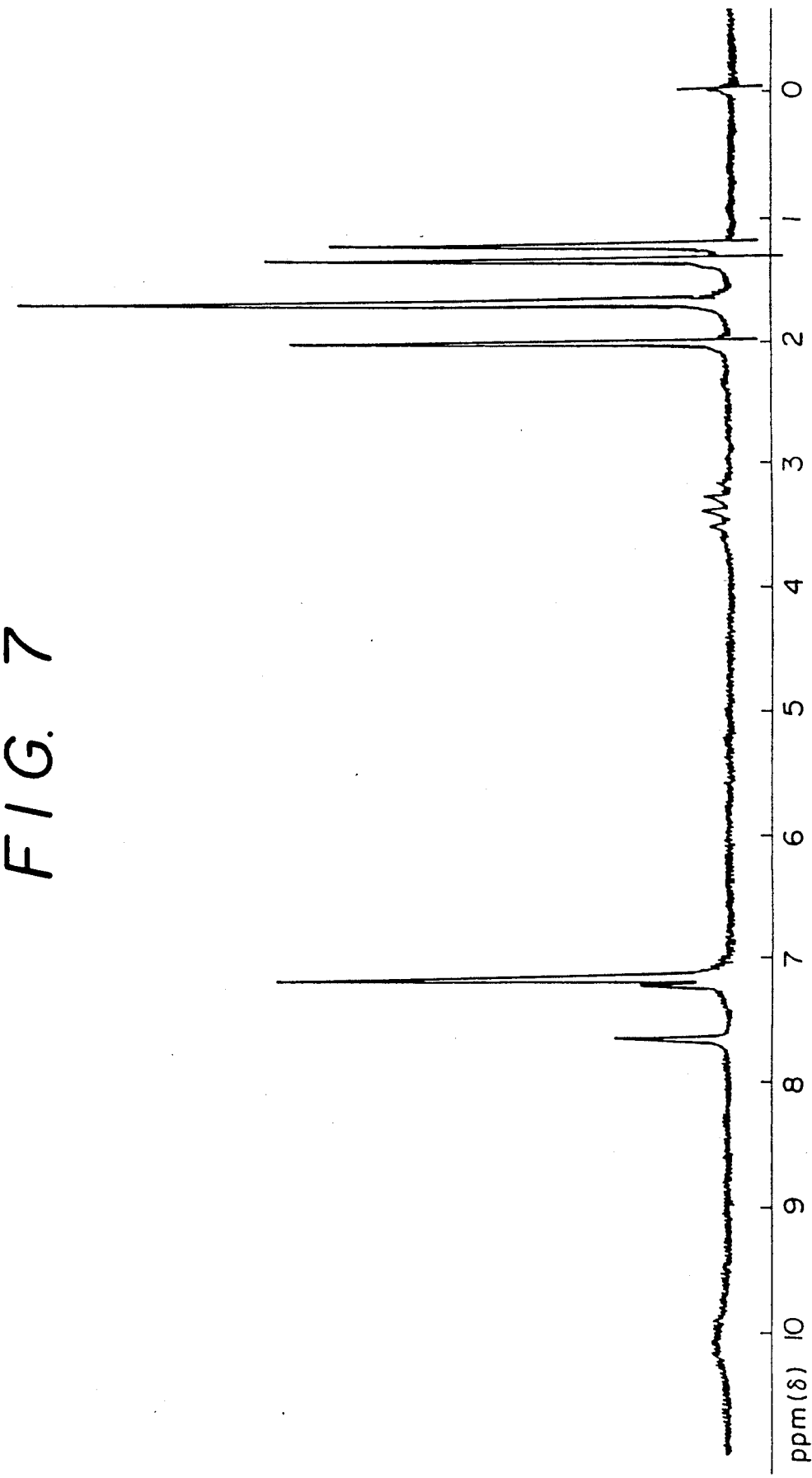

According to the same procedures used in Example 11-2, 210 g of white crystals were obtained from 335.5 g (1.25 mole) of 2-isopropyl-4-(α, α-dimethylbenzyl)-5-methylphenol obtained in Example 12-1. The melting point thereof was 174° C., its acid value was 179.1 (calculated value = 179.60) and the result of the NMR spectroscopic measurement was shown in FIG. 7. From these physical and chemical properties, the product is confirmed to be 3-isopropyl-5-(α, α-dimethylbenzyl)-6-methylsalicylic acid.

COMPARATIVE EXAMPLE 2

2-Methyl-4-(α, α-dimethylbenzyl)phenol was obtained from o-cresol and α-methylstyrene according to the same procedures used in Example 11-1 and then the product was treated according to the same procedures used in Example 11-2 to thus obtain 3-methyl-5-(α,α-dimethyllbenzyl)salicylic acid having a melting point of 180° C. and an acid value of 205.2 (calculated value = 207.55).

EXAMPLE 13

3.6-Dimethyl-5-(α, α-dimethylbenzyl)salicylic acid; 3-isopropyl-5-(α, α-dimethylbenzyl)-6-methylsalicylic acid; or 3-methyl-5-(α, α-dimethylbenzyl)salicylic acid obtained in Examples 11-2, 12-2 or Comparative Example 2 was neutralized with an aqueous solution of sodium hydroxide or morpholine to thus obtain an aqueous solution of a sodium or morpholine salt of each corresponding salicylic acid.

EXAMPLE 14

400 Grams of 25% aqueous solution of zinc sulfate were added to a flask having an inner volume of 2,000 ml and then each aqueous solution of the sodium salt obtained in Example 13, which had been diluted with water so that the sodium salt concentration thereof was 7%, was poured in the zinc sulfate solution with vigorous stirring. The flask was heated till the temperature of the content thereof was raised to 55° to 65° C. Since the particles of the contents became coarse at this stage, they were again cooled. The particles were filtered off, washed with water and then dried to thus obtain powder of zinc 3,6-dimethyl-5-( α,α-dimethylbenzyl)-salicylate, zinc 3-isopropyl-5-(α, α-dimethylbenzyl)-6-methylsalicylate or zinc 3-methyl-5-(α, α-dimethylbenzyl)salicylate, respectively. Each product had a zinc content of 10.1% (calculated value 10.34%), 9.42%

(calculated value =9.50%) or 10.3% (calculated value =10.82%).

An important feature of the nuclear substituted salicylic acids and the salts thereof according to the present invention is its excellent solubility in water and organic solvents and, therefore, they have enough practical value as bactericidal and germicidal agents, stabilizers for polymeric compounds and/or color developing agents for recording materials. These properties were practically determined and the results were listed in the following Table I.

The solubility was evaluated on the basis of the following four-stage evaluation standard. ⊙: solubility = not less than 50%; ○: solubility = not less than 20% to less than 50%; Δsolubility = not less than 5% to less than 20%; and x : solubility = less than 5%.

The transparency of polyvinyl chloride into which the compound of the present invention is incorporated is estimated by kneading a mixture comprising 100 parts by weight of polyvinyl chloride having a degree of polymerization of 1,300, 100 parts by weight of dioctyl phthalate and 3 parts by weight of the zinc nuclear substituted salicylate at 220° C. for 10 minutes and evaluating the transparency of the resultant compound based on the following four stage evaluation standard. ⊙: completely transparent; ○: almost transparency; Δ: slightly cloudy; x : severely cloudy.

Finally, the capacity of color development of the compounds of the present invention is determined by coating a paint solution containing the zinc nuclear substituted salicylate, which is prepared by adding an adhesive and the like, on paper so that the coated amount of the zinc nuclear substituted salicylate is 0.7 g/m², drying the coated paint and then carrying out printing on a pressure sensitive recording paper, i.e., wood-free paper to estimate the capacity of color development on the basis of the following four-stage evaluation standard. ⊙: very dense and high color developing speed; ○: dense; Δ: slightly dense; and x : no color development.

TABLE I

| Kind of Nuclear Substituted Salicylic Acid (Comp. Ex. No.) | Kind of Salt | Solubility in Water | Solubility in Toluene | Transparency of Polyvinyl Chloride | Color Developing Capacity |
|---|---|---|---|---|---|
| 1 | Free Acid | X | ○ | — | — |
| 1 | Sodium | ⊙ | — | — | — |
| 1 | Morpholine | ⊙ | ○ | — | — |
| 1 | Zinc | X | ⊙ | ⊙ | ○ |
| 2-2 | Free Acid | X | ⊙ | — | — |
| 2-2 | Sodium | ⊙ | — | — | — |
| 2-2 | Morpholine | ⊙ | ○ | — | — |
| 2-2 | Zinc | X | ⊙ | ⊙ | ⊙ |
| 3-2 | Free Acid | X | ○ | — | — |
| 3-2 | Sodium | ⊙ | — | — | — |
| 3-2 | Morpholine | ⊙ | ○ | — | — |
| 3-2 | Zinc | X | ⊙ | ⊙ | ⊙ |
| 4-3 | Free Acid | X | ⊙ | — | — |
| 4-3 | Sodium | ⊙ | — | — | — |
| 4-3 | Morpholine | ⊙ | ○ | — | — |
| 4-3 | Zinc | X | ⊙ | ⊙ | ⊙ |
| 5-3 | Free Acid | X | ⊙ | — | — |
| 5-3 | Sodium | ⊙ | — | — | — |
| 5-3 | Morpholine | ⊙ | ○ | — | — |
| 5-3 | Zinc | X | ⊙ | ⊙ | ⊙ |
| (1) | Free Acid | X | Δ | — | — |
| (1) | Sodium | ○ | — | — | — |
| (1) | Morpholine | ○ | Δ | — | — |
| (1) | Zinc | X | Δ | Δ | Δ |
| 11-2 | Free Acid | X | ○ | — | — |
| 11-2 | Sodium | ⊙ | — | — | — |
| 11-2 | Morpholine | ⊙ | ○ | — | — |
| 11-2 | Zinc | X | ⊙ | ⊙ | ⊙ |
| 12-2 | Free Acid | X | ⊙ | — | — |
| 12-2 | Sodium | ⊙ | — | — | — |
| 12-2 | Morpholine | ⊙ | ⊙ | — | — |
| 12-2 | Zinc | X | ⊙ | ⊙ | ⊙ |
| (2) | Free Acid | X | Δ | — | — |
| (2) | Sodium | ○ | — | — | — |
| (2) | Morpholine | ○ | Δ | — | — |
| (2) | Zinc | X | Δ | Δ | Δ |

What is claimed is:

1. A salt of a nuclear substituted salicylic acid represented by the following general formula (I):

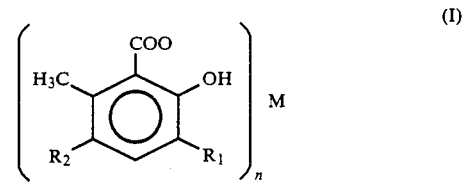

wherein $R_1$ represents a methyl group, an isopropyl group, a tert-butyl group, a tert-amyl group, a tert-hexyl group, a tert-octyl group, and α,α-dialkylbenzyl group or a nuclear substituted α,α-dialkylbenzyl group; $R_2$ represents a tert-butyl group, a tert-amyl group, a tert-hexyl group, a tert-octyl group, an α,α-dialkylbenzyl group or a nuclear substituted α,α-dialkylbenzyl group; M represents a metal atom; and n represents a valence number of the metal atom.

2. The salt of the nuclear substituted salicylic acid as set forth in claim 1, wherein the salt is a metal salt of a nuclear substituted salicylic acid selected from the group consisting of 3,6-dimethyl-5-(α,α-dimethylbenzyl) salicylic acid, 3-isopropyl-5-(α,α-dimethylbenzyl)-

6-methylsalicylic acid, 3,5-di-tert-butyl-6-methylsalicylic acid, 3-tert-butyl-5-(α,α-dimethylbenzyl)-6-methylsalicylic acid, 3,5-di-tert-amyl-6-methylsalicylic acid, 3-tert-octyl-5-tert-butyl-6-methylsalicylic acid and 3-(α,α-dimethylbenzyl)-5-tert-butyl-6-methylsalicylic acid.

3. The salt of the nuclear substituted salicylic acid as set forth in claim 1, wherein the salt is a polyvalent metal salt.

4. The salt of the nuclear substituted salicylic acid as set forth in claim 3, wherein the polyvalent metal salt is a zinc salt.

5. The salt of the nuclear substituted salicylic acid as set forth in claim 2, wherein the salt is a polyvalent metal salt.

6. The salt of the nuclear substituted salicylic acid as set forth in claim 5, wherein the polyvalent metal salt is a zinc salt.

* * * * *